United States Patent
Arluck et al.

(10) Patent No.: US 9,440,895 B2
(45) Date of Patent: Sep. 13, 2016

(54) ISOBARIC PRESSURE EXCHANGER CONTROLS IN AMINE GAS PROCESSING

(71) Applicant: Energy Recovery, Inc., San Leandro, CA (US)

(72) Inventors: James Lee Arluck, Hayward, CA (US); Jeremy Grant Martin, Oakland, CA (US); Prem Krish, Foster City, CA (US); John Sienkiewicz, San Mateo, CA (US)

(73) Assignee: ENERGY RECOVERY, INC., San Leandro, CA (US)

( * ) Notice: Subject to any disclaimer, the term of this patent is extended or adjusted under 35 U.S.C. 154(b) by 175 days.

(21) Appl. No.: 14/074,565

(22) Filed: Nov. 7, 2013

(65) Prior Publication Data

US 2014/0128656 A1     May 8, 2014

Related U.S. Application Data (60) Provisional application No. 61/724,056, filed on Nov. 8, 2012.

(51) Int. Cl.
*C07C 7/11*     (2006.01)
*B01D 3/00*     (2006.01)
(Continued)

(52) U.S. Cl.
CPC ................. *C07C 7/11* (2013.01); *B01D 3/009* (2013.01); *B01D 53/1425* (2013.01);
(Continued)

(58) Field of Classification Search
CPC ................................ B01D 3/009; C07C 7/11

USPC .......... 422/106, 110, 111, 119, 187; 585/860
See application file for complete search history.

(56) References Cited

U.S. PATENT DOCUMENTS

| | | | |
|---|---|---|---|
| 4,138,230 A | 2/1979 | Thompson | |
| 4,798,910 A | 1/1989 | Herrin | |

(Continued)

FOREIGN PATENT DOCUMENTS

| | | |
|---|---|---|
| CN | 202315685 | 7/2012 |
| FR | 2952710 A1 | 5/2011 |
| WO | 2012024804 A1 | 3/2012 |

OTHER PUBLICATIONS

A100 Amine Gas Treating System. Datasheet [online]. Exterran, Created: Dec. 8, 2012 [Retrieved on Feb. 15, 2014]. Retrieved from the Internet: <URL: http://www.exterran.com/Content/Docs/Products/A100-Amine-System-English-A4.pdf>, pp. 1-4.

(Continued)

*Primary Examiner* — Sean E Conley
(74) *Attorney, Agent, or Firm* — Fletcher Yoder, P.C.

(57) ABSTRACT

A system includes an amine gas processing controller that includes one or more tangible, non-transitory, machine-readable media collectively storing one or more sets of instructions and one or more processing devices configured to execute the one or more sets of instructions to operate a contactor to remove an acid gas from an untreated natural gas using an amine in a lean amine, output a treated natural gas, and output a rich amine stream, operate a regenerator to regenerate the amine in the rich amine stream, output the lean amine stream, and output the acid gas, transfer the rich amine stream from the contactor to the regenerator using an isobaric pressure exchanger (IPX), and transfer the lean amine stream from the regenerator to the contactor using the IPX.

21 Claims, 6 Drawing Sheets

(51) Int. Cl.
*B01D 53/14* (2006.01)
*C10L 3/10* (2006.01)
*F04F 13/00* (2009.01)

(52) U.S. Cl.
CPC .......... *B01D 53/1462* (2013.01); *C10L 3/102* (2013.01); *F04F 13/00* (2013.01); *B01D 2252/204* (2013.01); *B01D 2256/24* (2013.01); *Y02P 20/152* (2015.11)

(56) References Cited

U.S. PATENT DOCUMENTS 6,071,484 A 6/2000 Dingman et al.
2003/0201225 A1 10/2003 Josse et al.
2003/0205378 A1 11/2003 Wellington et al.
2009/0205496 A1 8/2009 Idem et al.
2011/0283690 A1 11/2011 Bollinger et al.

OTHER PUBLICATIONS

International Search Report and Written Opinion PCT/US13/69336 mailed on Mar. 19, 2014, pp. 1-11.
CN First Office Action and English Translation; Application No. CN201380069731.5; Dated Mar. 14, 2016; 12 pages.
EPO Search Report, 13753631.1-1451 /2916927 PCT/US2013069336, mailed Mar. 17, 2016, 4 pgs.
CA Office Action; Application No. CA 2,890,731; Dated May 9, 2016; 4 pages.

ISOBARIC PRESSURE EXCHANGER CONTROLS IN AMINE GAS PROCESSING

CROSS-REFERENCE TO RELATED APPLICATION

This application claims priority to and benefit of U.S. Provisional Patent Application No. 61/724,056, entitled "ISOBARIC ENERGY RECOVERY DEVICE (ERD) CONTROLS IN AMINE GAS PROCESSING," filed on Nov. 8, 2012, which is hereby incorporated by reference in its entirety for all purposes.

This application relates to U.S. Provisional Patent Application No. 61/724,031, entitled "ISOBARIC ENERGY RECOVERY DEVICE (ERD) IN AMINE GAS PROCESSING," filed on Nov. 8, 2012, which is herein incorporated by reference in its entirety for all purposes.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

The subject matter disclosed herein relates to natural gas processing, and, more particularly, to systems and methods for control of an isobaric pressure exchanger (IPX) during natural gas processing using water-based amine solutions.

Natural gas is a naturally occurring hydrocarbon gas mixture that may be combusted to provide energy or used as a chemical feedstock in the manufacture of plastics and other organic chemicals. Virgin natural gas (e.g., untreated natural gas), as it emerges from natural geologic reservoirs, contains varying amounts of sour gases, particularly carbon dioxide and hydrogen sulfide, also referred to as acid gases. Carbon dioxide reduces the calorific value of the natural gas and hydrogen sulfide may transform into sulfur dioxide, sulfur trioxide, and/or sulfuric acid. An amine gas treating process has been developed to remove these sour gas components from virgin natural gas, thus converting the virgin natural gas into sweet gas (e.g., treated natural gas) that is suitable for combustion in domestic and industrial applications. Unfortunately, large amounts of energy may be expended in pressurizing the amine solutions used in the amine gas treating process, which is then lost (e.g., not recovered) when the sour gases are stripped from the amine solutions.

BRIEF DESCRIPTION OF THE DRAWINGS

Various features, aspects, and advantages of the present invention will become better understood when the following detailed description is read with reference to the accompanying figures in which like characters represent like parts throughout the figures, wherein.

DETAILED DESCRIPTION OF SPECIFIC EMBODIMENTS

One or more specific embodiments of the present invention will be described below. These described embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

As discussed in detail below, the disclosed embodiments relate generally to natural gas processing, and particularly to an amine gas processing system that processes natural gas using water-based amine solutions (e.g., an alkylamine or amine) and an isobaric pressure exchanger (IPX). For example, the amine gas processing system may include a contactor that removes an acid gas from an untreated natural gas (e.g., virgin natural gas) using an amine in a lean amine stream, thereby generating treated natural gas (e.g., sweet gas) and a rich amine stream. The treated natural gas may be combusted to provide energy or used as a chemical feedstock. The amine gas processing system may also include a regenerator that regenerates the amine in the rich amine stream, thereby generating the lean amine stream and the acid gas. The carbon dioxide and hydrogen sulfide present in the acid gas may be used as feedstocks for other processes, such as a Claus process to produce elemental sulfur or a carbon capture and storage process. The amine gas processing system may also include an IPX that transfers the rich amine stream from the contactor to the regenerator and transfers the lean amine stream from the regenerator to the contactor. Isobaric may be defined as same pressure or constant pressure. Thus, the IPX may include chambers wherein the pressures of two volumes of a liquid may equalize, as described in detail below. In some embodiments, the pressures of the two volumes of liquid may not completely equalize. Thus, the IPX may not only operate isobarically, but also substantially isobarically (e.g., wherein the pressures equalize within approximately +/−1, 2, 3, 4, 5, 6, 7, 8, 9, or 10 percent of each other). In certain embodiments, a first pressure of the rich amine stream may be greater than a second pressure of the lean amine stream. For example, the first pressure may be between approximately 6,000 kPa to 8,000 kPa, 6,500 kPa to 7,500 kPa, or 6,750 kPa to 7,250 kPa greater than the second pressure. Thus, the IPX may be used to transfer pressure from the rich amine stream to the lean amine stream. The amine gas processing system may also include a controller system or controller to operate one or more components of the system, as described in detail below.

Use of such embodiments of amine gas processing system that include the IPX may provide several advantages compared to other amine gas processing systems that lack the IPX. For example, energy losses associated with a rich amine flow control valve may be avoided while simultaneously enabling control of the contactor level and reducing the operating cost of the amine gas processing system. In addition, in amine gas processing systems constructed according to the disclosed embodiments, a reduction of capital cost may be achieved through the reduction in size or number of pumps, variable frequency drives (VFDs), recirculation loops, control valves, related equipment, and so forth. Moreover, in situations where the operating capacity of an existing amine gas processing system is limited by electrical power constraints, such as availability, laddered power costs, rationing, or any combination thereof, implementation of the disclosed embodiments may alleviate the electrical power constraints, thereby enabling increased throughput and profitability. Further, the disclosed embodiments may help increase the throughput and profitability of the amine gas processing system by increasing the flow rate of the lean amine stream to the contactor. In addition, use of the disclosed embodiments may reduce the costs associated with expanding the capacity of an existing amine gas processing system, such as by adding an additional processing train or contactor.

Figure 1:
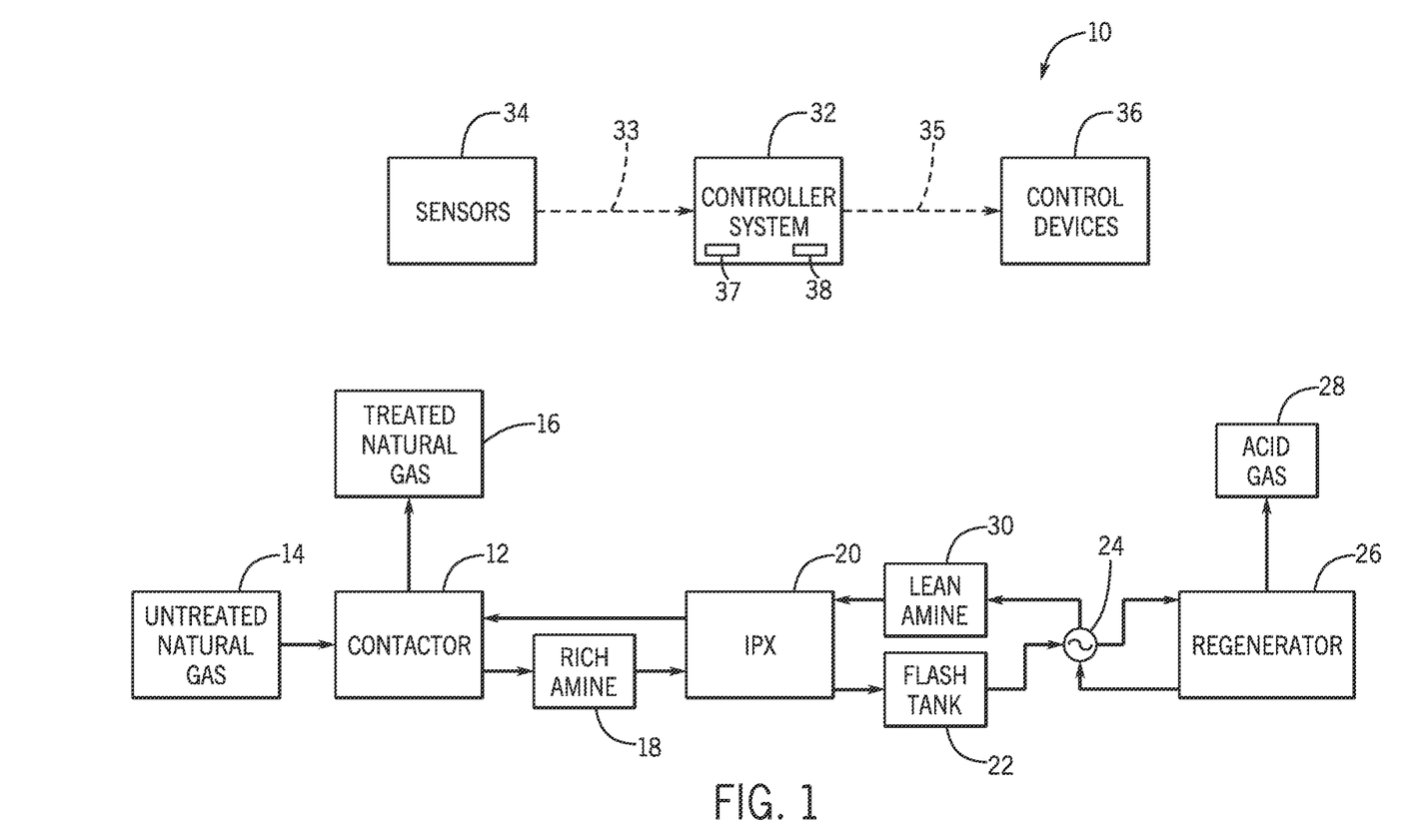
FIG. 1 is a schematic diagram of an embodiment of an amine gas processing system using an isobaric pressure exchanger (IPX)

FIG. 1 is a schematic diagram of an embodiment of an amine gas processing system 10 that may be used for natural gas processing. As shown in FIG. 1, a contactor 12 receives an untreated natural gas 14 (e.g., virgin natural gas), for example, at the bottom of the contactor 12. A lean amine stream 30 (e.g., a liquid) may be fed to the top of the contactor 12. As the untreated natural gas 14 moves upwards in the contactor 12, the natural gas 14 makes intimate contact with the down-flowing lean amine 30. As a result of this interaction within the contactor 12, the sour gases (e.g., acid gases) in the untreated natural gas 14 leave the gas phase stream and enter the liquid phase amine solution stream. Thus, a treated natural gas 16 (e.g., sweet gas) substantially free of the sour gases may leave through the top of the contactor 12.

The untreated natural gas 14 may enter the contactor 12 at pressures up to approximately 8,270 kPa and at a temperature of approximately 30 degrees Celsius. Throughout the following discussion, the term "high-pressure" may refer to pressures associated with operation of the contactor 12 (e.g., up to approximately 6,895 kPa, 7,585 kPa, or 8,270 kPa). The lean amine 30 may enter the contactor 12 at temperatures approximately 3 to 20 degrees Celsius, 4 to 15 degrees Celsius, or 5 to 12 degrees Celsius greater than the inlet temperature of the untreated natural gas 14 to help reduce or prevent condensation of heavier hydrocarbons from the untreated natural gas 14. Because of the exothermicity of the sour gas absorption reactions, the amine solution heats up within the contactor 12 and a rich amine stream 18, laden with sour gas, may leave the bottom of the contactor 12 at temperatures approaching approximately 60 degrees Celsius. The exiting rich amine stream 18 then enters an IPX 20, which reduces the pressure of the rich amine stream 18 to between approximately 475 kPa to 730 kPa, 500 kPa to 715 kPa, or 515 kPa to 690 kPa. The low-pressure rich amine stream 18 is then routed by the IPX 20 through a flash tank 22, where any hydrocarbon gases are allowed to flash off and be recovered, and then to a rich/lean heat exchanger 24 and onwards to a regenerator 26, where the sour gases are stripped from the rich amine 18 through the application of heat. Thus, the rich/lean heat exchanger 24 is used to transfer heat from the lean amine 30 leaving the regenerator 26 to the rich amine 18 entering the regenerator 26. Acid gases 28 (e.g., sour gases) leave the top of the regenerator 26 after being released from the amine solution stream as a result of heating in the regenerator 26. The lean amine 30 coming from the regenerator 26 at pressures between approximately 475 kPa to 730 kPa, 500 kPa to 715 kPa, or 515 kPa to 690 kPa passes through the rich/lean heat exchanger 24 and enters the IPX 20, wherein the pressure of the lean amine stream 30 is increased to the contactor pressure of up to approximately 8,270 kPa. Throughout the following discussion, the term "low-pressure" may refer to pressures associated with operation of the regenerator 26 (e.g., between approximately 475 kPa to 730 kPa, 500 kPa to 715 kPa, or 515 kPa to 690 kPa).

As used herein, the isobaric pressure exchanger (IPX) 20 may be generally defined as a device that transfers fluid pressure between a high-pressure inlet stream (e.g., the rich amine 18 from the contactor 12) and a low-pressure inlet stream (e.g., the lean amine 30 from the regenerator 26) at efficiencies in excess of approximately 50%, 60%, 70%, or 80% without utilizing centrifugal technology. In this context, high pressure refers to pressures greater than the low pressure. The low-pressure inlet stream of the IPX 20 may be pressurized and exit the IPX 20 at high pressure (e.g., at a pressure greater than that of the low-pressure inlet stream), and the high-pressure inlet stream may be depressurized and exit the IPX at low pressure (e.g., at a pressure less than that of the high-pressure inlet stream). Additionally, the IPX 20 may operate with the high-pressure fluid directly applying a force to pressurize the low-pressure fluid, with or without a fluid separator between the fluids. Examples of fluid separators that may be used with the IPX 20 include, but are not limited to, pistons, bladders, diaphragms and the like. In certain embodiments, isobaric pressure exchangers may be rotary or non-rotary devices. Rotary isobaric pressure exchangers (IPXs) 20, such as those manufactured by Energy Recovery, Inc. of San Leandro, Calif., may not have any separate valves, since the effective valving action is accomplished internal to the device via the relative motion of a rotor with respect to end covers, as described in detail below with respect to FIGS. 2-6. Non-rotary IPXs 20 may include separate valves that govern the flow of the high-pressure and low-pressure fluid streams into and out of the device. Both rotary and non-rotary IPXs 20 may be designed to operate with internal pistons to isolate fluids and transfer pressure with little mixing of the inlet fluid streams. Non-rotary IPXs 20 may also be designed with bladders and/or diaphragms, which may provide the same functionality as internal pistons (e.g., isolating fluids and transferring pressure). Reciprocating IPXs 20 may include a piston moving back and forth in a cylinder for transferring pressure between the fluid streams. Any IPX 20 or plurality of IPXs 20 may be used in the disclosed embodiments, such as, but not limited to, rotary IPXs, non-rotary IPXs, reciprocating IPXs, bladder-based IPXs, or any combination thereof. While the discussion with respect to certain embodiments may refer to rotary IPXs 20, it is understood that any IPX 20 or plurality of IPXs 20 may be substituted for the rotary IPX 20 in any of the disclosed embodiments. In addition, the IPX 20 may be disposed on a skid separate from the other components of the amine gas processing system 10, which may be desirable in situations in which the IPX 20 is added to an existing system 10.

As shown in FIG. 1, a controller system (one or more controllers) 32 may be used to control one or more aspects of the amine gas processing system 10. For example, one or more sensors 34 disposed throughout the system 10 may provide input signals 33 to the controller system 32, which may then generate output signals 35 (e.g., control signals) to one or more control devices 36 disposed throughout the system 10. The sensors 34 may provide input signals 33 indicative of, but not limited to, temperature, pressure, flow rate, composition, material properties, liquid level, speed, and so forth. The control devices 36 may include, but are not limited to, control valves, isolation valves, variable frequency drives (VFDs), motors, actuators, and so forth. For example, the control devices 36 may include motor-driven valves, actuator-driven valves, and so forth. Specific examples of the sensors 34 and control devices 36 that may be used in conjunction with the IPX 20 of the system 10 are discussed in detail below.

The controller system 32 may include a distributed control system (DCS), a programmable logic controller (PLC) with Human Machine Interface (HMI), or any computer-based workstation that is fully or partially automated. For example, the controller system 32 may be any device employing a general purpose or an application-specific processor 37, both of which may generally include memory circuitry 38 for storing instructions related to pressure differentials and flow rates, for example. The processor 37 may include one or more processing devices, and the memory circuitry 38 may include one or more tangible, non-transitory (i.e., not signals), machine-readable media collectively storing instructions executable by the processor 37 to perform the methods and control actions described herein. Such machine-readable media can be any available media that can be accessed by the processor 37 or by any general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by the processor 37 or by any general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions comprise, for example, instructions and data which cause the processor 37 or any general purpose computer, special purpose computer, or special purpose processing machines to perform a certain function or group of functions. In certain embodiments, the amine gas processing system 10 may include one or more sensors 34 and control devices 36 at various locations of the system 10, and one or more controller systems (or controllers) 32 coupling these sensors 34 and control devices 36 to govern operation of the system 10. For simplicity, the sensors 34 and control devices 36 are shown separate from the components of the system 10 in the schematic diagram of FIG. 1, however, the sensors 34 and control devices 36 are distributed and disposed throughout various locations within the system 10, as described in detail below.

Figure 2:
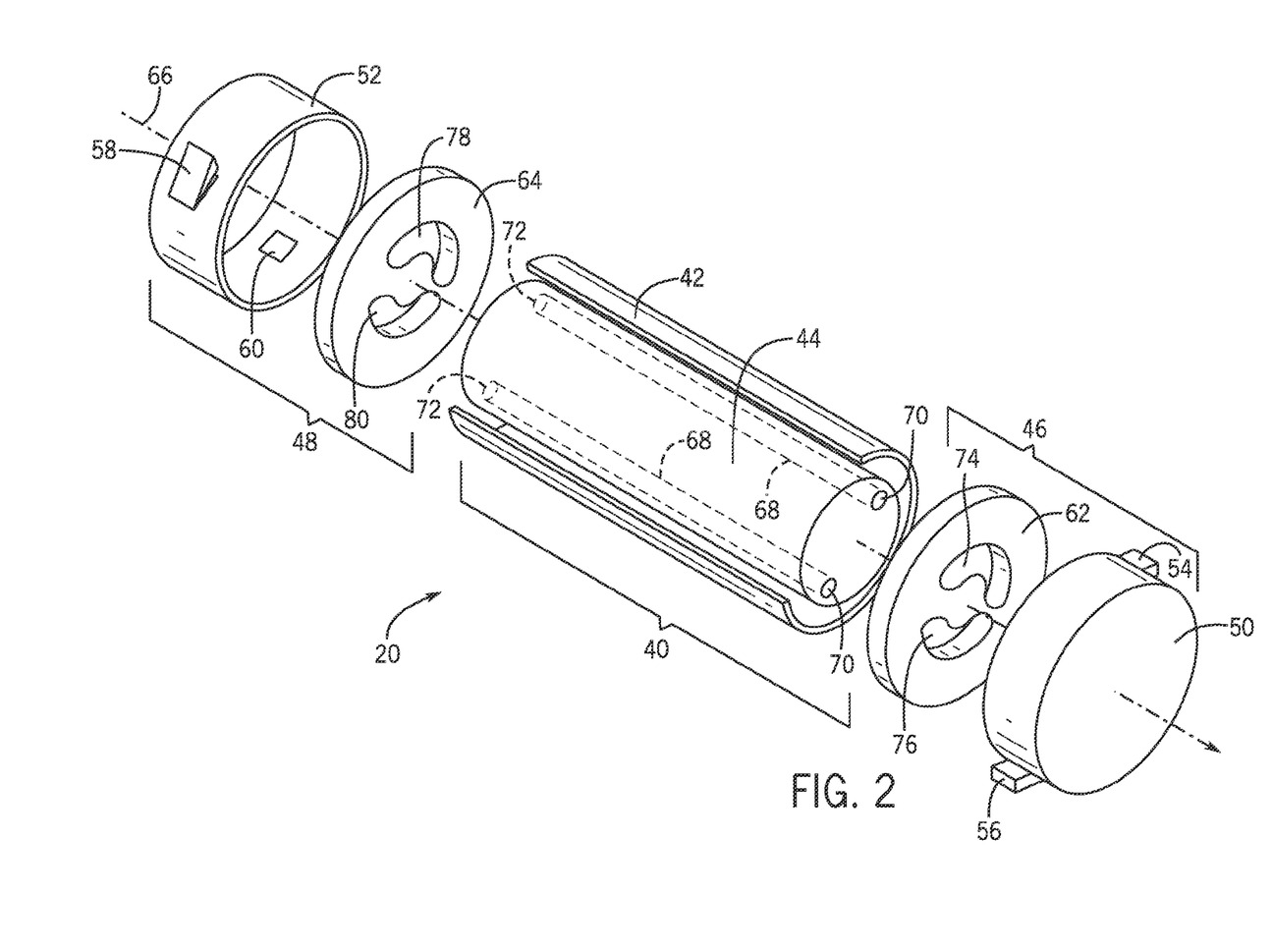
FIG. 2 is an exploded perspective view of an embodiment of a rotary IPX.

FIG. 2 is an exploded view of an embodiment of a rotary IPX 20. In the illustrated embodiment, the rotary IPX 20 may include a generally cylindrical body portion 40 that includes a housing 42 and a rotor 44. The rotary IPX 20 may also include two end structures 46 and 48 that include manifolds 50 and 52, respectively. Manifold 50 includes inlet and outlet ports 54 and 56 and manifold 52 includes inlet and outlet ports 60 and 58. For example, inlet port 54 may receive the high-pressure rich amine stream 18 from the contactor 12 and the outlet port 56 may be used to route the low-pressure rich amine stream 18 to the regenerator 26. Similarly, inlet port 60 may receive the low-pressure lean amine stream 30 from the regenerator 26 and the outlet port 58 may be used to route the high-pressure lean amine stream 30 to the contactor 12. The end structures 46 and 48 include generally flat end plates 62 and 64, respectively, disposed within the manifolds 50 and 52, respectively, and adapted for liquid sealing contact with the rotor 44. The rotor 44 may be cylindrical and disposed in the housing 42, and is arranged for rotation about a longitudinal axis 66 of the rotor 44. The rotor 44 may have a plurality of channels 68 extending substantially longitudinally through the rotor 44 with openings 70 and 72 at each end arranged symmetrically about the longitudinal axis 66. The openings 70 and 72 of the rotor 44 are arranged for hydraulic communication with the end plates 62 and 64, and inlet and outlet apertures 74 and 76, and 78 and 80, in such a manner that during rotation they alternately hydraulically expose liquid at high pressure and liquid at low pressure to the respective manifolds 50 and 52. The inlet and outlet ports 54, 56, 58, and 60, of the manifolds 50 and 52 form at least one pair of ports for high-pressure liquid in one end element 46 or 48, and at least one pair of ports for low-pressure liquid in the opposite end element, 48 or 46. The end plates 62 and 64, and inlet and outlet apertures 74 and 76, and 78 and 80 are designed with perpendicular flow cross sections in the form of arcs or segments of a circle.

With respect to the IPX 20, the plant operator has control over the extent of mixing between the rich and lean amine streams 18 and 30, which may be used to improve the operability of the amine gas processing system 10. For example, varying the proportions of the rich and lean amine streams 18 and 30 entering the IPX 20 allows the plant operator to control the amount of fluid mixing within the system 10. The three characteristics of the IPX 20 that affect mixing are: the aspect ratio of the rotor channels 68, the short duration of exposure between the rich and lean amine streams 18 and 30, and the creation of a liquid barrier (e.g., an interface) between the rich and lean amine streams 18 and 30 within the rotor channels 68. First, the rotor channels 68 are generally long and narrow, which stabilizes the flow within the IPX 20. In addition, the amine streams 18 and 30 may move through the channels 68 in a plug flow regime with very little axial mixing. Second, in certain embodiments, at a rotor speed of approximately 1200 RPM, the time of contact between the rich and lean amine streams 18 and 30 may be less than approximately 0.15 seconds, 0.10 seconds, or 0.05 seconds, which again limits mixing of the streams 18 and 30. Third, a small portion of the rotor channel 68 is used for the exchange of pressure between the streams 18 and 30. Therefore, a volume of amine remains in the channel 68 as a barrier between the rich and lean amine streams 18 and 30. All these mechanisms may limit mixing within the IPX 20.

In addition, because the IPX 20 is configured to be exposed to the rich amine stream 18 and the lean amine stream 30, certain components of the IPX 20 may be made from materials compatible with the components of the streams 18 and 30. For example, in certain embodiments, the housing 42 may be made from a duplex stainless steel. Other components of the IPX 20 may also be made from materials suitable for use with the rich and lean amine streams 18 and 30. In addition, certain components of the IPX 20 may be configured to be physically compatible with other components of the amine gas processing system 10. For example, the ports 54, 56, 58, and 60 may comprise flanged connectors to be compatible with other flanged connectors present in the piping of the amine gas processing system 10. In other embodiments, the ports 54, 56, 58, and 60 may comprise threaded or other types of connectors.

FIGS. 3-6 are exploded views of an embodiment of the rotary IPX 20 illustrating the sequence of positions of a single channel 68 in the rotor 44 as the channel 68 rotates through a complete cycle, and are useful to an understanding of the rotary IPX 20. It is noted that FIGS. 3-6 are simplifications of the rotary IPX 20 showing one channel 68 and the channel 68 is shown as having a circular cross-sectional shape. In other embodiments, the rotary IPX 20 may include a plurality of channels 68 with different cross-sectional shapes. Thus, FIGS. 3-6 are simplifications for purposes of illustration, and other embodiments of the rotary IPX 20 may have configurations different from that shown in FIGS. 3-6. As described in detail below, the rotary IPX 20 facilitates a hydraulic exchange of pressure between two liquids by putting them in momentary contact within a rotating chamber. In certain embodiments, this exchange happens at a high speed that results in very high efficiency with very little mixing of the liquids.

Figures 3, 4, 5, 6:
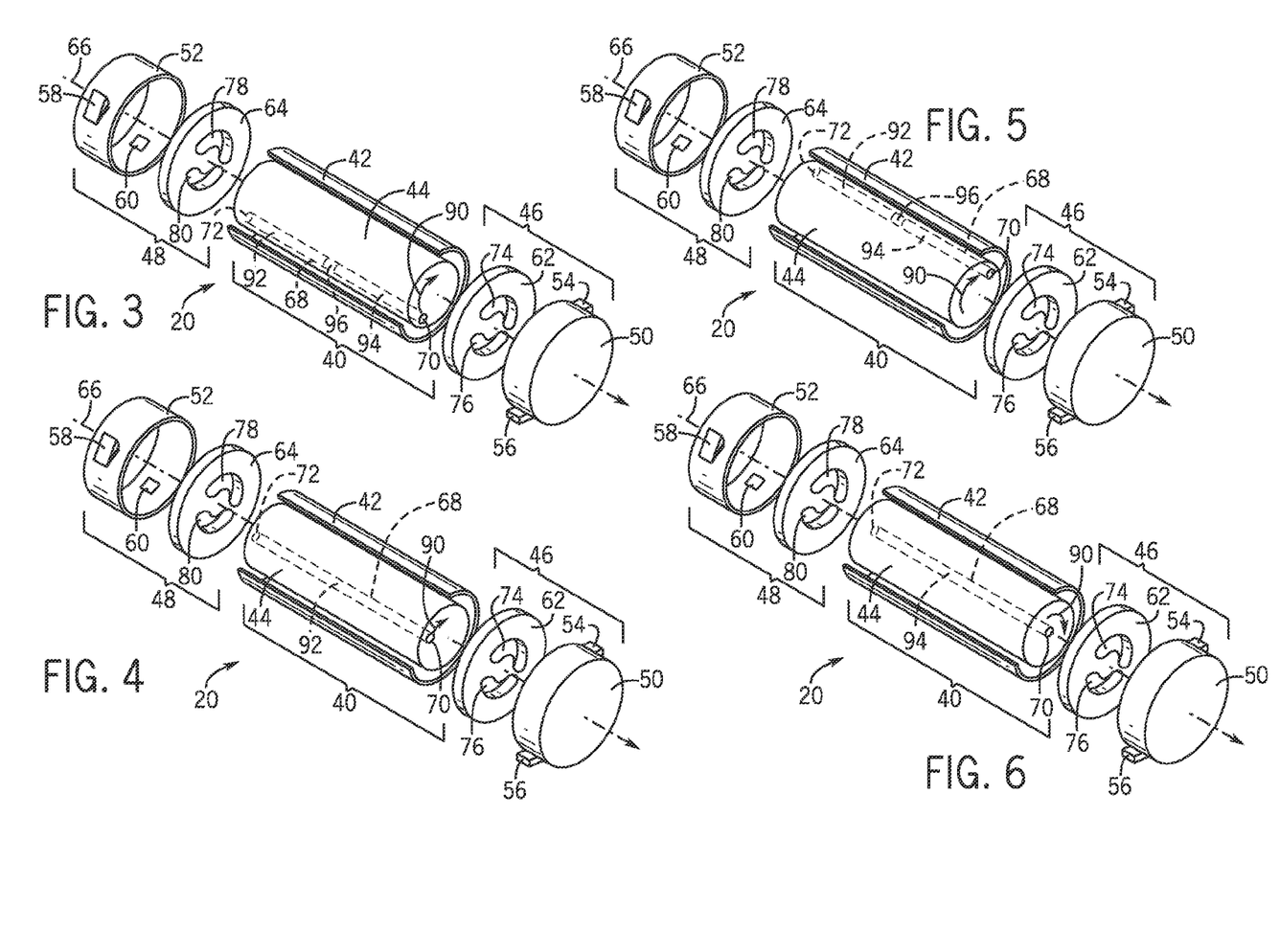
FIG. 3 is an exploded perspective view of an embodiment of a rotary IPX in a first operating position.
FIG. 4 is an exploded perspective view of an embodiment of a rotary IPX in a second operating position.
FIG. 5 is an exploded perspective view of an embodiment of a rotary IPX in a third operating position.
FIG. 6 is an exploded perspective view of an embodiment of a rotary IPX in a fourth operating position.

In FIG. 3, the channel opening 70 is in hydraulic communication with aperture 76 in endplate 62 and therefore with the manifold 50 at a first rotational position of the rotor 44 and opposite channel opening 72 is in hydraulic communication with the aperture 80 in endplate 64, and thus, in hydraulic communication with manifold 52. As discussed below, the rotor 44 rotates in the clockwise direction indicated by arrow 90. As shown in FIG. 3, low-pressure lean amine 92 (e.g., lean amine 30 from the regenerator 26) passes through end plate 64 and enters the channel 68, where it pushes rich amine 94 (e.g., rich amine 18 from the contactor 12) out of the channel 68 and through end plate 62, thus exiting the rotary IPX 20. The lean amine 92 and rich amine 94 contact one another at an interface 96 where minimal mixing of the liquids occurs because of the short duration of contact. The interface 96 is a direct contact interface because the lean amine 92 directly contacts the rich amine 92.

In FIG. 4, the channel 68 has rotated clockwise through an arc of approximately 90 degrees, and outlet 72 is now blocked off between apertures 78 and 80 of end plate 64, and outlet 70 of the channel 68 is located between the apertures 74 and 76 of end plate 62 and, thus, blocked off from hydraulic communication with the manifold 50 of end structure 46. Thus, the low-pressure lean amine 92 is contained within the channel 68.

In FIG. 5, the channel 68 has rotated through approximately 180 degrees of arc from the position shown in FIG. 3. Opening 72 is in hydraulic communication with aperture 78 in end plate 64 and in hydraulic communication with manifold 52, and the opening 70 of the channel 68 is in hydraulic communication with aperture 74 of end plate 62 and with manifold 50 of end structure 46. The liquid in channel 68, which was at the pressure of manifold 52 of end structure 48, transfers this pressure to end structure 46 through outlet 70 and aperture 74, and comes to the pressure of manifold 50 of end structure 46. Thus, high-pressure rich amine 94 (e.g., rich amine 18 from the contactor 12) pressurizes and displaces the lean amine 92.

In FIG. 6, the channel 68 has rotated through approximately 270 degrees of arc from the position shown in FIG. 3, and the openings 70 and 72 of channel 68 are between apertures 74 and 76 of end plate 62, and between apertures 78 and 80 of end plate 64. Thus, the high-pressure rich amine 94 is contained within the channel 68. When the channel 68 rotates through approximately 360 degrees of arc from the position shown in FIG. 3, the lean amine 92 displaces the rich amine 94, restarting the cycle.

Figure 7:
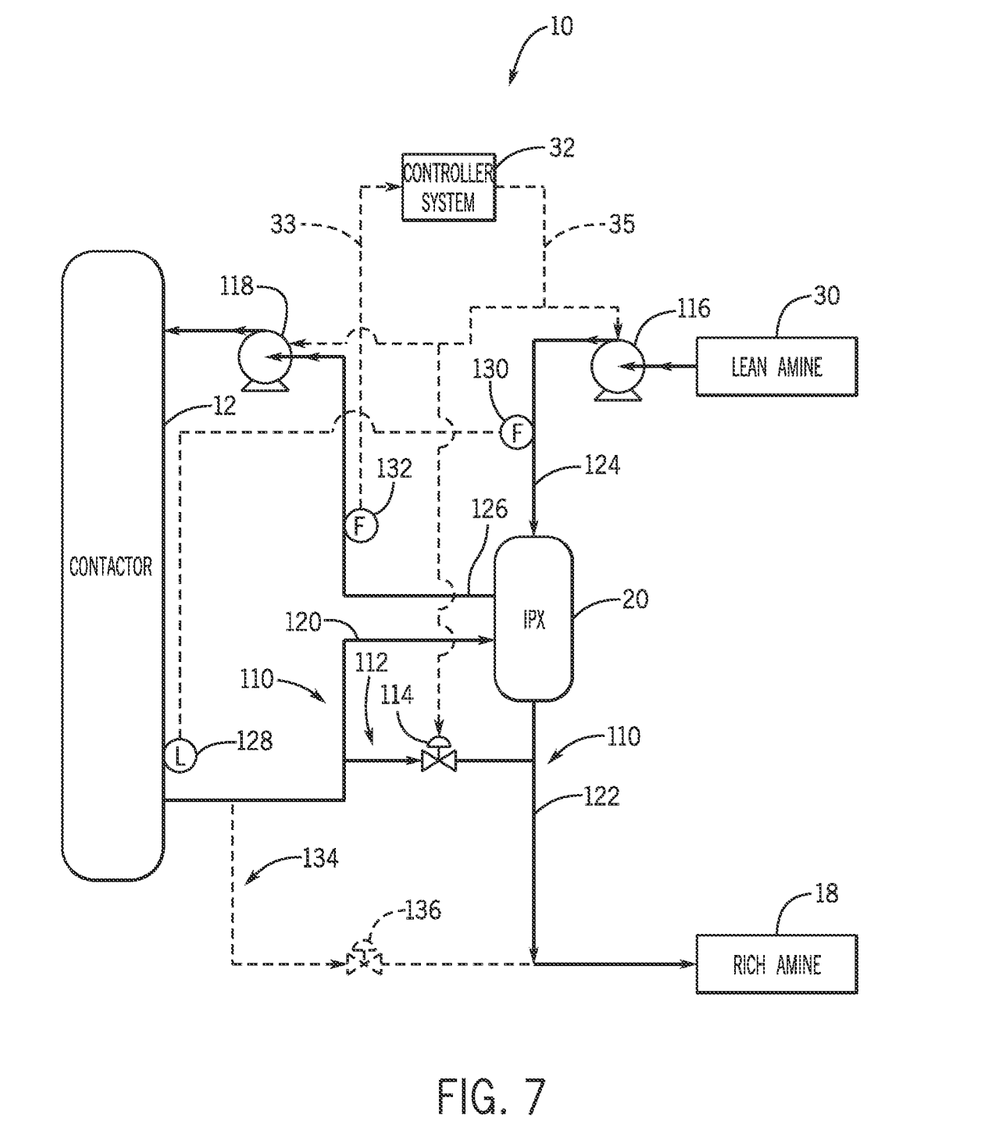
FIG. 7 is a diagram of an embodiment of an amine gas processing system with an IPX.

FIG. 7 is a diagram of an embodiment of the amine gas processing system 10 with the IPX 20 in parallel with a control valve 114. Specifically, the IPX 20 may be disposed in a normal loop 110 that routes the rich amine 18 from the contactor 12 to the regenerator 26, as described in detail below. In addition, a bypass loop 112 may include a level control valve 114 for routing the rich amine 18 from the contactor 12 to the regenerator 26 without passing through the IPX 20. Thus, once the high-pressure rich amine 18 leaves the contactor 12, the full flow does not go to the IPX 20. Instead, a portion of the flow of rich amine 18 enters the IPX 20 and the remainder of the flow goes through the level control valve 114. The flows of rich amine 18 are recombined upstream of the flash tank 22, thus maintaining approximately constant pressure (e.g., within approximately +/−1, 2, 3, 4, 5, 6, 7, 8, 9, or 10% of each other) and flow in the system. The level control valve 114 may help maintain a desired amine solution liquid level in the bottom of the contactor 12 to help prevent any gas from exiting the contactor 12 through the bottom end liquid phase piping. In addition, the level control valve 114 may be used by the plant operator, who interacts with the controller system 32 through a human-machine-interface (HMI) for example, to vary the amount of rich amine 18 entering the IPX 20. Although use of the level control valve 114 may lower the overall efficiency of the system 10 as a portion of the pressure energy is lost at the level control valve 114, it allows the plant operator to have finer control over the system 10 by using the level control valve 114 to maintain level control of the contactor 12 to avoid gas from exiting the bottom of the contactor 12, for example. As with the IPX 20, the level control valve 114 may reduce the pressure of the rich amine stream 18 to between approximately 475 kPa to 730 kPa, 500 kPa to 715 kPa, or 515 kPa to 690 kPa. However, in contrast to the IPX 20, pressure energy that is relieved in the level control valve 114 is essentially wasted. In other words, the IPX 20 uses the pressure energy from reducing the pressure of the rich amine 18 to increase the pressure of the lean amine entering the contactor 12. Thus, use of the level control valve 114 may be reduced to improve the overall efficiency of amine gas processing system 10. In certain embodiments, the IPX 20 and the level control valve 114 may completely replace a flow control valve 136 located in a flow control valve bypass loop 134, which is then omitted, thereby eliminating the waste of pressure energy by the flow control valve 136. In further embodiments, the flow control valve 136 may be present, but normally remains closed. Thus, although the flow control valve 136 may not normally be used, the valve 136 may be opened when desired. By using the IPX 20 to either eliminate or reduce use of the flow control valve 136, the amine gas processing system 10 may use much less energy to pressurize the lean amine 30 entering the contactor 12 compared to systems that do not include the IPX 20.

As shown in FIG. 7, in certain embodiments, there are four fluid connections to the IPX 20, namely a rich amine inlet 120 (high pressure), a rich amine outlet 122 (low pressure), a lean amine inlet 124 (low pressure), and a lean amine outlet 126 (high pressure). As described above, the lean amine 30 enters the IPX 20 at low pressure and is pressurized by the incoming high-pressure rich amine 18 coming from the bottom of the contactor 12 at a pressure approximately equal to that of the contactor 12 (e.g., up to approximately 6,895 kPa, 7,585 kPa, or 8,270 kPa). The lean amine 30 leaves the IPX 20 at high pressure and may pass through a circulation pump 118 before entering the top of the contactor 12. The circulation pump 118 may be used to pressurize the lean amine 30 to a pressure substantially equal (e.g., within approximately +/−1, 2, 3, 4, 5, 6, 7, 8, 9, or 10 percent) to that of the contactor 12 and may be used to overcome an inefficiency of the IPX 20 and/or pressure losses in lines between the regenerator 26 and the contactor 12. The rich amine 18 leaves the IPX 20 at low pressure (e.g., between approximately 475 kPa to 730 kPa, 500 kPa to 715 kPa, or 515 kPa to 690 kPa) and is sent to the flash tank 22 and regenerator 26. Low-pressure lean amine 30 leaves the regenerator 26 at low pressure and enters the IPX 20, thereby restarting the cycle. In certain embodiments, one or more pumps 116 may be used to pressurize the lean amine 30 before reaching the IPX 20. For example, because of certain process conditions, a low-pressure feed pump 116 may be added to the amine gas processing system 10 prior to the lean amine 30 entering the IPX 20. The low-pressure feed pump 116 may be configured to increase the pressure of the lean amine 30 flowing to the IPX 20 to a value greater than the pressure of the regenerator 26, but less than the pressure of the contactor 12. In further embodiments, the amine gas processing system 10 may include none, one, or both of the pumps 116 and 118.

In the illustrated embodiment of FIG. 7, the controller system 32 may be used to control one or more aspects of the amine gas processing system 10. For example, the controller system 32 may receive the input signals 33 from various sensors 34, such as a contactor level sensor 128, a lean amine regenerator flow rate sensor 130, a lean amine ERD flow rate sensor 132, or any combination thereof. Based on the information conveyed by the input signals 33, the controller system 32 may generate output signals 35 to various control devices 36, such as the level control valve 114, a VFD for the low-pressure feed pump 116, a VFD for the circulation pump 118, or any combination thereof. Specifically, the controller system 32 may implement one or more of the processes described below.

In addition, the controller system 32 may be used to vary the proportions of the rich and lean amine streams 18 and 30 entering the IPX 20, which allows the plant operator to control the amount of fluid mixing within the amine gas processing system 10. One way to reduce mixing in the IPX 20 is to supply excess lean amine 30 to clear the channels 68 of any residual rich amine fluid 18, which may be referred to as overflush. Overflush may reduce mixing in the IPX 20 depending on the amount of overflush. Zero overflush may be referred to as "balanced flow" when the inlet flow rate of the lean amine 30 to the IPX 20 substantially equals the outlet flow rate of the lean amine 30. The amount of overflush may either be set manually using independent (e.g., separate from the controller system 32) controllers for both pumps 116 and 118, or automatically set using a flow balancing function within the controller system 32 using linked or slaved VFDs.

Although one embodiment of the use of the controller system 32 with the amine gas processing system 10 is illustrated in FIG. 7, the controller system 32 may be used with other configurations of the system 10 that include the IPX 20. For example, the level control valve 114 may not be disposed in parallel with the IPX 20. Instead, the level control valve 114 may be disposed in series with and downstream of the IPX 20. In other words, the level control valve 114 may be disposed between the rich amine outlet 122 and the flash tank 22. In other embodiments, an additional pump (e.g., a high-pressure pump) may be disposed in a lean amine bypass loop around the IPX 20 or in series with either the circulation pump 118 or the low-pressure feed pump 116. The high-pressure pump may be configured to increase the pressure of the lean amine 30 to a value substantially equal (e.g., within approximately +/−1, 2, 3, 4, 5, 6, 7, 8, 9, or 10 percent) to the pressure of the contactor 12. In further embodiments, a pump may be integrated with the IPX 20 and used to replace either the circulation pump 118 or the low-pressure feed pump 116 (e.g., a pump configured to increase the pressure of the lean amine 30 flowing to the IPX 20 to a value greater than the pressure of the regenerator 26, but less than the pressure of the contactor 12). In other words, the IPX 20 may be permanently coupled to the integrated within the housing of the IPX 20. In any of these embodiments, the controller system 32 may be used to provide desired operating conditions of the amine gas processing system 10 using one or more of the processes discussed in detail below.

Figure 8:
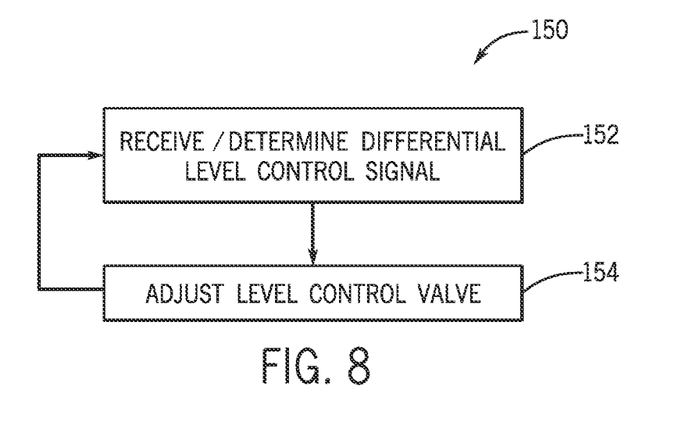
FIG. 8 a flow chart of an embodiment of a process for operating a level control valve of an amine gas processing system with an IPX.

FIG. 8 a flow chart of an embodiment of a process 150 for operating the level control valve 114 of the amine gas processing system 10. In a step 152, the controller system 32 receives a differential level control signal (e.g., a signal indicative of a difference between two liquid level values or a difference between a desired liquid level and an actual liquid level) from the system 10 (e.g., high or low). For example, the differential level control signal may indicate whether the liquid level (e.g., liquid level of the rich amine 18) in the contactor 12 should be increased or decreased. Alternatively, the controller system 32 may receive a setpoint input from the plant operator and a level signal from the contactor level sensor 128 indicative of the liquid level of the contactor 12, from which the differential level control signal (e.g., difference between the setpoint input and the level signal) may be computed by the controller system 32. For example, if the level signal from sensor 128 is greater than the setpoint input, the differential level control signal (e.g., a high-level differential signal) may indicate that the liquid level in the contactor 12 should be decreased. Similarly, if the level signal of the contactor 12 is less than the setpoint input, the differential level control signal (e.g., a low-level differential signal) may indicate that the liquid level in the contactor 12 should be increased. In a step 154, the controller system 32 adjusts the level control valve 114 position based on a control algorithm, such as a proportional-integral-derivative (PID) algorithm. The PID algorithm may adjust the valve 114 closed to raise the liquid level in the contactor 12 for a low-level differential signal, and may adjust the valve 114 open to lower the liquid level in the contactor 12 for a high-level differential signal. Specifically, to lower the liquid level in the contactor 12, the level control valve 114 bypasses rich amine 18 flow around the IPX 20, allowing increased flow on the rich amine 18 side of the IPX 20 without affecting flow on the lean amine 30 side, thus lowering the liquid level of the contactor 12 without causing a change in the rich/lean flow balance within the IPX 20. To raise the level of fluid in the contactor 12, the level control valve 114 closes, reducing or eliminating the bypass flow around the IPX 20 through the bypass loop 112. The process 150 may then repeat by returning to the step 152. Thus, the IPX 20 may function to transfer most of the rich amine 18 from the contactor 12 to the regenerator 26 while also transferring pressure energy to the lean amine 30, thereby reducing pressure energy losses associated with the level control valve 114, which is used primarily for controlling the liquid level of the contactor 12.

Figure 9:
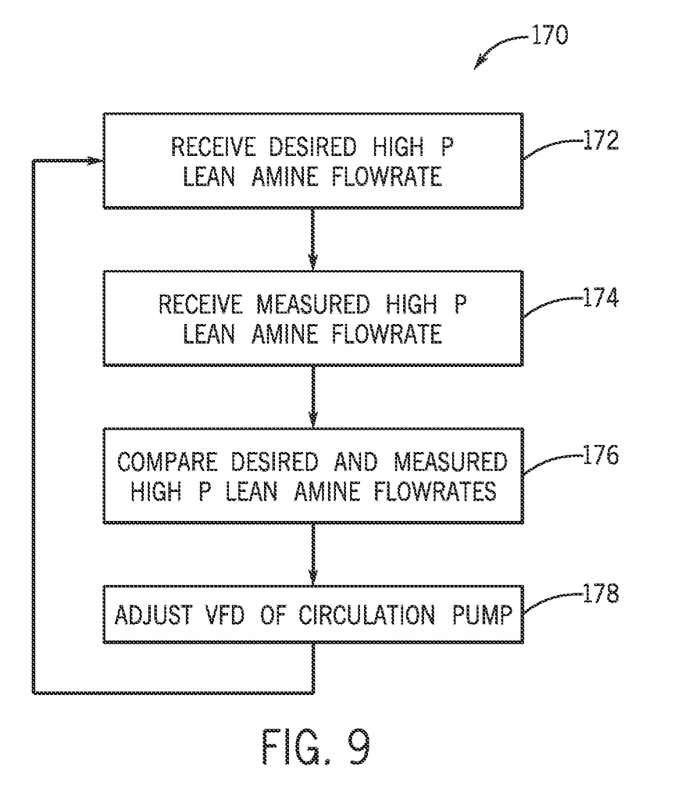
FIG. 9 a flow chart of an embodiment of a process for operating a variable frequency drive (VFD) of a circulation pump of an amine gas processing system with an IPX.

FIG. 9 a flow chart of an embodiment of a process 170 for operating the VFD of the circulation pump 118 of the amine gas processing system 10. In a step 172, the controller system 32 receives a desired high-pressure lean amine 30 flow rate to the contactor 12 from the plant operator or from an input from the controller system 32, which may be input into the controller system 32 through a plant HMI. In a step 174, the controller system 32 receives a measured high-pressure lean amine 30 flow rate as indicated by the lean amine ERD flow rate sensor 132. In a step 176, the controller system 32 compares the plant operator's desired lean amine 30 flow value with the measured lean amine 30 flow value as measured by sensor 132. In a step 178, the controller system 32 adjusts the VFD of the circulation pump 118 to change the speed of the pump 118 using, for example, PID controls. The process 170 may then repeat by returning to the step 172. In other words, the lean amine ERD flow rate sensor 132 may provide a new flow rate, the controller system 32 compares it to the user-desired lean amine 30 flow value, and the controller system 32 continually adjusts the VFD of the circulation pump 118 and circulation pump speed of the pump 118 until the desired flow of lean amine 30 to the contactor 12 is achieved. The PID loop may remain active to maintain lean amine 30 flow control throughout the process 170. Thus, the process 170 may be helpful in achieving desired conditions within the contactor 12.

Figure 10:
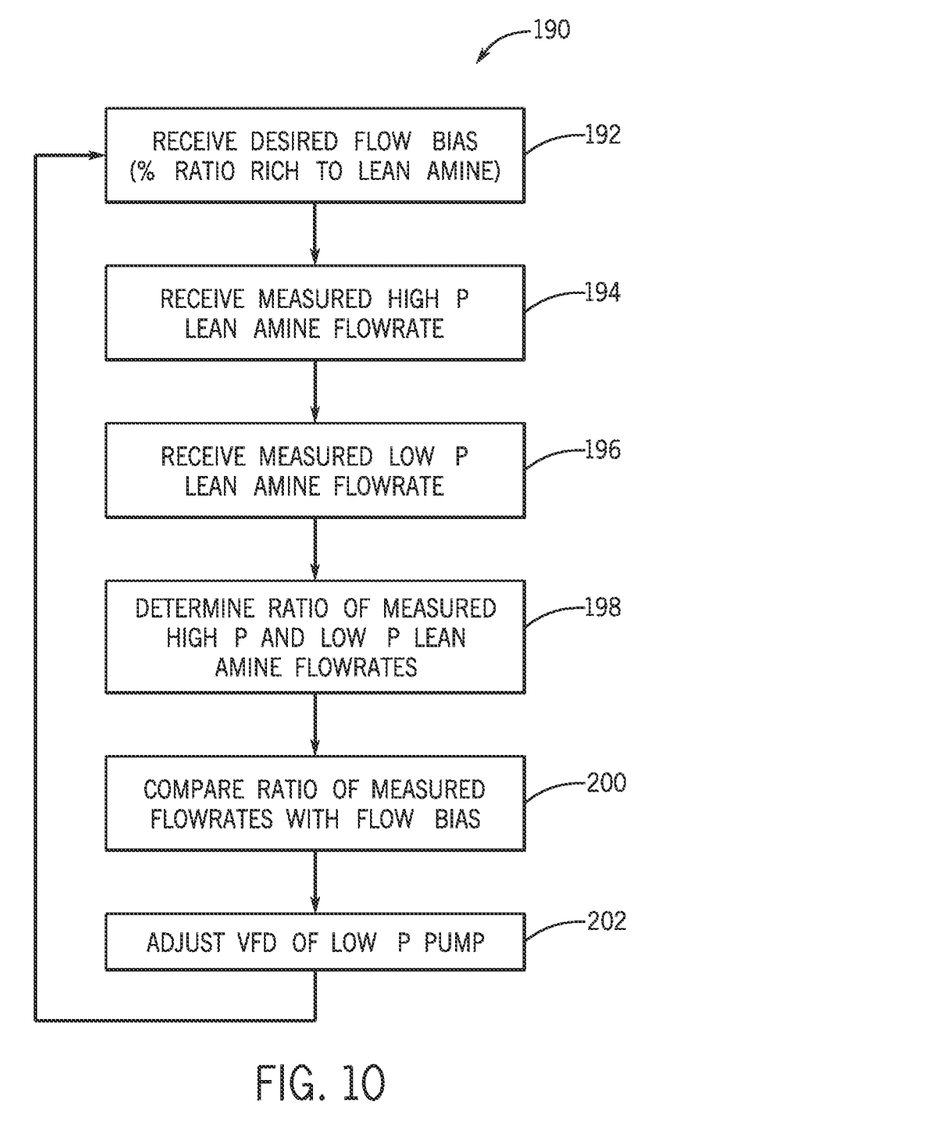
FIG. 10 a flow chart of an embodiment of a process for operating a VFD of a low-pressure pump of an amine gas processing system with an IPX.

FIG. 10 a flow chart of an embodiment of a process 190 for operating the VFD of the low-pressure feed pump 116 of the amine gas processing system 10. In a step 192, the plant operator or from an input from the controller system 32 provides a desired flow bias (e.g., difference between rich and lean amine flow rates) input to the controller system 32, e.g., expressed as a percentage (%) ratio of rich amine 18 flow rate to lean amine 30 flow rate. In determining the flow bias, the flow rate of the rich amine 18 may refer to the flow rate of the rich amine 18 flowing to the regenerator and the flow rate of the lean amine 30 may refer to the flow rate of the lean amine 30 flowing to the contactor 12. In a step 194, the controller system 32 receives the measured high-pressure lean amine 30 flow rate as indicated by the lean amine ERD flow rate sensor 132, but does not adjust the VFD for the circulation pump 118. In a step 196, the controller system 32 receives a measured low-pressure lean amine 30 flow rate as indicated by the lean amine regenerator flow rate sensor 130. In a step 198, the controller system 32 determines a flow ratio of the measured high-pressure lean amine 30 flow rate to the measured low-pressure lean amine 30 flow rate. In a step 200, the controller system 32 compares this flow ratio to the desired flow bias input of the step 192. In a step 202, the controller system 32 changes the speed of the low-pressure feed pump 116 via its VFD and the PID control loop for the pump 116. The process 190 may then repeat by returning to the step 192. In other words, the new flow rate of the measured low-pressure lean amine 30 flow rate is provided by the lean amine regenerator flow rate sensor 130 and the measured flow ratio is compared to the desired flow bias input of the step 192. The VFD of the low-pressure feed pump 116 and the low-pressure feed pump speed are continually adjusted by the controller system 32 until the desired flow bias is achieved. The PID loop may remain active to maintain the rich/lean amine flow bias within user specifications. As discussed above, varying the flow rate of the lean amine 30 entering the IPX 20 through the lean amine inlet 124 affects the rich/lean amine flow bias through the process of overflush. For example, increasing the flow rate of the lean amine 30 entering the IPX 20 may increase the overflush (e.g., more of the rich amine 18 is flushed out of the channels 68 by the lean amine 30), thereby decreasing the rich/lean amine flow bias. Similarly, decreasing the flow rate of the lean amine 30 entering the IPX 20 may decrease the overflush, thereby increasing the rich/lean amine flow bias. Thus, the process 190 may be helpful in achieving a desired amount of mixing of the lean amine 30 with the rich amine 18, which may affect operating conditions within the contactor 12.

As described above, certain embodiments of the amine gas processing system 10 may include a controller system 32 with instructions to operate the contactor 12 to remove the acid gas 28 from the untreated natural gas 14 using an amine in the lean amine stream 30, thereby generating the treated natural gas 16 and the rich amine stream 18. The controller system 32 with may also include instructions to operate the regenerator to regenerate the amine in the rich amine stream 18, thereby generating the lean amine stream 30 and the acid gas 28. The controller system 32 with may also include instructions to use the IPX 20 to transfer the rich amine stream 18 from the contactor 12 to the regenerator 26 and to transfer the lean amine 30 from the regenerator 26 to the contactor 12. The IPX 20 may also transfer pressure from the rich amine stream 18 entering the IPX 20 to the lean amine stream 30 leaving the IPX 20. Thus, use of the controller system 32 with the IPX 20 may enable control of the liquid level of the contactor 12, while reducing the operating cost for the amine gas processing system 10. In addition, use of the controller system 32 with the IPX 20 may provide the plant operator with additional flexibility in operating the system 10, reduce capital costs associated with the system 10, increase the operating capacity of the system 10, increase the profitability of the system 10, and/or reduce costs associated with expanding the system 10.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system, comprising:
an amine gas processing controller, comprising:
one or more tangible, non-transitory, machine-readable media collectively storing one or more sets of instructions; and
one or more processing devices configured to execute the one or more sets of instructions to:
transfer a rich amine stream from a contactor to a regenerator using an isobaric pressure exchanger (IPX); and
transfer a lean amine stream from the regenerator to the contactor using the IPX;
wherein the IPX transfers pressure energy from the rich amine stream to the lean amine stream.

2. The system of claim 1, wherein the one or more processing devices are configured to execute the one or more sets of instructions to:
operate the contactor to remove an acid gas from an untreated natural gas using an amine in the lean amine, output a treated natural gas, and output the rich amine stream; and
operate the regenerator to regenerate the amine in the rich amine stream, output the lean amine stream, and output the acid gas.

3. The system of claim 1, wherein the one or more processing devices are configured to execute the one or more sets of instructions to:
receive or determine a differential level control signal; and
adjust, based on the differential level control signal, a level control valve disposed in a rich amine bypass loop around the IPX to control a level of the rich amine stream in the contactor.

4. The system of claim 1, wherein the one or more processing devices are configured to execute the one or more sets of instructions to:
receive a desired high-pressure lean amine flow rate signal;
receive a measured high-pressure lean amine flow rate signal;
compare the desired high-pressure lean amine flow rate signal with the measured high-pressure lean amine flow rate signal to obtain a first comparison; and
adjust, based on the first comparison, a first variable frequency drive (VFD) of a circulation pump configured to transfer the lean amine stream from the IPX to the contactor.

5. The system of claim 1, wherein the one or more processing devices are configured to execute the one or more sets of instructions to:
receive a desired flow bias input;
receive a measured high-pressure lean amine flow rate signal;
receive a measured low-pressure lean amine flow rate signal;
determine a ratio of the measured high-pressure lean amine flow rate signal to the measured low-pressure lean amine flow rate signal;
compare the ratio with the desired flow bias input to obtain a second comparison; and
adjust, based on the second comparison, a second VFD of a first pump configured to transfer the lean amine stream from the regenerator to the IPX.

6. A system, comprising:
an amine gas processing system, comprising:
a contactor configured to remove an acid gas from an untreated natural gas using an amine in a lean amine stream, output a treated natural gas, and output a rich amine stream;
a regenerator configured to regenerate the amine in the rich amine stream, output the lean amine stream, and output the acid gas;
an isobaric pressure exchanger (IPX) configured to transfer the rich amine stream from the contactor to the regenerator, to transfer the lean amine stream from the regenerator to the contactor, and to transfer pressure energy from the rich amine stream to the lean amine stream; and
a controller system configured to control operation of the amine gas processing system by adjusting a control device based on an input signal from a sensor.

7. The system of claim 6, wherein the sensor comprises a contactor level sensor configured to provide the input signal indicative of a level of the rich amine stream in the contactor.

8. The system of claim 6, wherein the sensor comprises a first lean amine flow rate sensor configured to provide the input signal indicative of a lean amine regenerator flow rate of the lean amine stream from the regenerator to the IPX.

9. The system of claim 6, wherein the sensor comprises a second lean amine flow rate sensor configured to provide the input signal indicative of a lean amine ERD flow rate of the lean amine stream from the IPX to the contactor.

10. The system of claim 6, wherein the control device comprises a level control valve disposed in a rich amine bypass loop around the IPX, wherein the level control valve is configured to adjust a level of the rich amine stream in the contactor.

11. The system of claim 6, wherein the control device comprises a circulation pump configured to adjust a lean amine ERD flow rate of the lean amine stream from the IPX to the contactor.

12. The system of claim 6, wherein the control device comprises a first pump configured to adjust a lean amine regenerator flow rate of the lean amine stream from the regenerator to the IPX.

13. The system of claim 6, wherein the IPX comprises at least one of a rotary IPX, a non-rotary IPX, a reciprocating IPX, or a bladder-based IPX, or any combination thereof.

14. The system of claim 6, wherein the IPX is configured to transfer pressure from the rich amine stream entering the IPX at a first pressure to the lean amine stream leaving the IPX at a second pressure, wherein the first pressure is greater than the second pressure.

15. The system of claim 6, wherein an outer housing of the IPX comprises duplex stainless steel, and the IPX comprises flanged connectors.

16. A method, comprising:
removing an acid gas from an untreated natural gas using an amine in a lean amine stream in a contactor;
generating a treated natural gas and a rich amine stream from the contactor;
regenerating the amine in the rich amine stream in a regenerator;
generating the lean amine stream and the acid gas from the regenerator;
transferring the rich amine stream from the contactor to the regenerator using an isobaric pressure exchanger (IPX);
transferring the lean amine stream from the regenerator to the contactor using the IPX;
transferring pressure energy from the rich amine stream to the lean amine stream using the IPX;
adjusting a first flow rate of the rich amine stream using a first control device; and
adjusting a second flow rate of the lean amine stream using a second control device.

17. The method of claim 16, comprising adjusting the first flow rate based at least in part on a differential level control signal comprising a difference between a desired liquid level and an actual liquid level.

18. The method of claim 16, comprising adjusting the second flow rate of the lean amine stream from the IPX to the contactor based at least in part on a comparison of a desired high-pressure lean amine flow rate and a measured high-pressure lean amine flow rate.

19. The method of claim 16, comprising adjusting the second flow rate of the lean amine stream from the regenerator to the IPX based at least in part on a comparison of a ratio of a measured high-pressure lean amine flow rate to a measured low-pressure lean amine flow rate and a desired flow bias input comprising a difference between a desired flow rate of the lean amine stream to the contactor and a desired flow rate of the rich amine to the regenerator.

20. The method of claim 16, wherein adjusting the first flow rate of the rich amine stream using the first control device comprises adjusting a level control valve disposed in a rich amine bypass loop around the IPX.

21. The method of claim 16, wherein adjusting the second flow rate of the lean amine stream using the second control device comprises at least one of adjusting a first variable frequency drive (VFD) of a circulation pump configured to transfer the lean amine stream from the IPX to the contactor, or adjusting a second VFD of a first pump configured to transfer the lean amine stream from the regenerator to the IPX, or any combination thereof.

* * * * *